US012667265B2

(12) United States Patent
Lee et al.

(10) Patent No.: US 12,667,265 B2
(45) Date of Patent: Jun. 30, 2026

(54) ELECTRONIC DEVICE AND METHOD OF ESTIMATING SKIN SURFACE TEMPERATURE USING THE SAME

(71) Applicant: SAMSUNG ELECTRONICS CO., LTD., Suwon-si (KR)

(72) Inventors: So Young Lee, Suwon-si (KR); Sang Kyu Kim, Suwon-si (KR); Bok Soon Kwon, Suwon-si (KR); Sungho Kim, Suwon-si (KR); Ho Taik Lee, Suwon-si (KR); Hong Soon Rhee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 598 days.

(21) Appl. No.: 18/124,814

(22) Filed: Mar. 22, 2023

(65) Prior Publication Data

US 2024/0164651 A1 May 23, 2024

(30) Foreign Application Priority Data

Nov. 18, 2022 (KR) ........................ 10-2022-0155673

(51) Int. Cl.
*A61B 5/0205* (2006.01)
*A61B 5/00* (2006.01)
(Continued)

(52) U.S. Cl.
CPC .......... *A61B 5/02055* (2013.01); *A61B 5/681* (2013.01); *A61B 5/021* (2013.01);
(Continued)

(58) Field of Classification Search
CPC ..... A61B 5/02055; A61B 5/681; A61B 5/021; A61B 5/02416; A61B 2562/0271; A61B 2562/04
See application file for complete search history.

(56) References Cited

U.S. PATENT DOCUMENTS

| | | | |
|---|---|---|---|
| 7,249,883 B2 | 7/2007 | Kuroda et al. | |
| 7,299,090 B2 | 11/2007 | Koch | |

(Continued)

FOREIGN PATENT DOCUMENTS

| | | |
|---|---|---|
| CN | 215227566 U | 12/2021 |
| JP | 5898204 B2 | 4/2016 |

(Continued)

OTHER PUBLICATIONS

Communication dated Oct. 27, 2023, issued by the European Patent Office in counterpart European Application No. 23171017.9.

*Primary Examiner* — William J Levicky
*Assistant Examiner* — Jessandra F Hough
(74) *Attorney, Agent, or Firm* — Sughrue Mion, PLLC

(57) ABSTRACT

An electronic device may include: a first temperature sensor configured to measure a first temperature when an object comes into contact with a contact surface of a main body of the electronic device; a second temperature sensor spaced apart from the first temperature sensor in a direction opposite the contact surface and configured to measure a second temperature; and a processor configured to detect a temperature change due to heat generation inside the main body, and estimate skin surface temperature based on the first temperature, the second temperature, and the temperature change.

15 Claims, 15 Drawing Sheets

(51) Int. Cl.
   *A61B 5/021*   (2006.01)
   *A61B 5/024*   (2006.01)
(52) U.S. Cl.
   CPC ... *A61B 5/02416* (2013.01); *A61B 2562/0271*
        (2013.01); *A61B 2562/04* (2013.01)

(56) References Cited

U.S. PATENT DOCUMENTS

| | | |
|---|---|---|
| 9,357,929 B2 | 6/2016 | Paquet |
| 9,699,546 B2 | 7/2017 | Qian et al. |
| 9,952,105 B2 | 4/2018 | Shimizu et al. |
| 10,209,209 B2 | 2/2019 | Ikeda et al. |
| 10,368,811 B1 | 8/2019 | Bajaj et al. |
| 10,765,409 B2 | 9/2020 | Lafon et al. |
| 11,109,764 B2 | 9/2021 | Bongers et al. |
| 11,224,344 B2 | 1/2022 | Ellis et al. |
| 11,246,493 B2 | 2/2022 | Kim et al. |
| 2016/0238463 A1 | 8/2016 | Bieberich et al. |
| 2016/0258823 A1 | 9/2016 | Shimizu et al. |
| 2019/0175024 A1 | 6/2019 | Lan et al. |
| 2019/0350462 A1 | 11/2019 | Biederman et al. |
| 2021/0123819 A1 | 4/2021 | Seyama et al. |
| 2021/0169417 A1* | 6/2021 | Burton ................. A61B 5/4857 |
| 2022/0386878 A1 | 12/2022 | Li et al. |
| 2022/0395185 A1 | 12/2022 | Lee et al. |
| 2023/0036809 A1 | 2/2023 | Lee et al. |
| 2023/0066222 A1 | 3/2023 | Lee et al. |

FOREIGN PATENT DOCUMENTS

| | | |
|---|---|---|
| KR | 10-1877550 B1 | 7/2018 |
| WO | 2021057873 A1 | 4/2021 |

\* cited by examiner

ELECTRONIC DEVICE AND METHOD OF ESTIMATING SKIN SURFACE TEMPERATURE USING THE SAME

CROSS-REFERENCE TO RELATED APPLICATION(S)

This application claims priority from Korean Patent Application No. 10-2022-0155673, filed on Nov. 18, 2022, in the Korean Intellectual Property Office, the disclosure of which is incorporated herein by reference in its entirety.

BACKGROUND

1. Field

Apparatuses and methods consistent with example embodiments relate to estimating skin surface temperature using an electronic device.

2. Description of the Related Art

Temperature sensors may be classified into two types: contact type sensors and non-contact type sensors. Contact type sensors may detect changes in electrical resistance, via a Resistance Temperature Detector (RTD), a thermistor, or the like, or may detect electromotive force via thermocouple or the like. Non-contact type sensor, on the other hand, may measure body temperature by detecting infrared rays radiating from a body surface, and examples of the non-contact type sensors include a thermopile, a micro-bolometer.

When using a contact type sensor to measure skin surface temperature, there is a difference between a temperature measured by a temperature sensor in a device placed in proximity to the skin surface, and the actual temperature on the skin's contact surface. In addition, heat generating components are included in the device may affect the temperature sensor depending on the type and position of the heat generating components. Accordingly, there has been a demand for improving the estimation accuracy of the skin surface temperature.

SUMMARY

According to an aspect of the present disclosure, an electronic device may include: a first temperature sensor configured to measure a first temperature when an object comes into contact with a contact surface of a main body of the electronic device; a second temperature sensor spaced apart from the first temperature sensor in a direction opposite the contact surface and configured to measure a second temperature; and a processor configured to detect a temperature change due to heat generation inside the main body, and estimate skin surface temperature based on the first temperature, the second temperature, and the temperature change.

The processor may be further configured to detect the temperature change due to the heat generation inside the main body based on at least one of a variation in the first temperature compared to a first reference temperature, and a variation in the second temperature compared to a second reference temperature.

A first condition may be satisfied when the variation in the first temperature is greater than or equal to a predetermined first threshold value, and a second condition may be satisfied when variation in the second temperature is greater than or equal to a predetermined second threshold value. In response to either one or both of the first condition and the second condition is satisfied, the processor may be further configured to determine that the temperature change has occurred due to the heat generation inside the main body.

In response to the temperature change being detected, the processor may be further configured to determine the first temperature and the second temperature as outliers.

In response to the first temperature and the second temperature being determined as the outliers, the processor may be further configured to terminate measurement of the first temperature and the second temperature, or guide re-measurement of the first temperature and the second temperature after a lapse of a predetermined period of time.

The electronic device may further include a third temperature sensor disposed inside the main body and configured to measure a third temperature when heat is generated inside the main body. The processor may be further configured to detect the temperature change due to the heat generation inside the main body based on at least one of a ratio of a difference between the first temperature and the second temperature and a difference between the first temperature and the third temperature, and a ratio of the difference between the first temperature and the second temperature and a difference between the second temperature and the third temperature.

In response to the ratio of the difference between the first temperature and the second temperature and the difference between the first temperature and the third temperature being greater than or equal to a predetermined third threshold value when the first temperature is higher than the third temperature, or in response to the ratio of the difference between the first temperature and the second temperature and the difference between the first temperature and the third temperature being less than or equal to a predetermined fourth threshold value when the third temperature is higher than the first temperature, the processor may be further configured to determine that the temperature change has occurred due to the heat generation inside the main body.

Upon determining that the temperature change has occurred, the processor may be further configured to correct the first temperature and the second temperature based on the third temperature.

The processor may be further configured to correct each of the first temperature and the second temperature by subtracting from each of the first temperature and the second temperature in the main body, heat that is transferred from a heat generating component to the first temperature sensor and the second temperature sensor, respectively.

The processor may be further configured to estimate the skin surface temperature based on a difference between the corrected first temperature and the corrected second temperature.

Based on arrangement of the first temperature sensor and the second temperature sensor, the processor may be further configured to classify heat generating components that causes the heat generation in the main body into a plurality of groups, and determine the third threshold value and the fourth threshold value differently for each of the plurality of groups.

Among the plurality of groups, the processor may be further configured to determine a group of heat generating components which are in operation when the skin surface temperature is measured, among the plurality of groups of the heat generating components, and apply a threshold value corresponding to the determined group.

The third temperature sensor may be attached to a heat generating component that generates heat at a predetermined temperature inside the main body.

When the main body of the electronic device is in contact with the skin surface of the object, the first temperature sensor may be disposed at a distance of 5 mm or less from the skin surface.

According to another aspect of the present disclosure, a wearable device may include: a main body including: a first temperature sensor disposed in the main body at a position spaced apart from a contact surface of the wearable device by a first distance; a second temperature sensor disposed in the main body at a position spaced apart from the contact surface of the wearable device by a second distance, which is greater than the first distance; and a processor configured to estimate skin surface temperature based on a first temperature measured by the first temperature sensor and a second temperature measured by the second temperature sensor.

The wearable device may further include a third temperature sensor disposed in the main body at a position spaced apart from the contact surface by a third distance, which is greater than the second distance.

The processor may be further configured to correct the first temperature and the second temperature based on a third temperature measured by the third temperature sensor when heat is generated inside the main body, and estimate the skin surface temperature based on the corrected first temperature and the corrected second temperature.

The third distance may be 65 mm or less.

The main body may further include a photoplethysmogram (PPG) sensor configured to measure a bio-signal of a user when the wearable device is worn by the user, and the processor may be further configured to estimate blood pressure based on the bio-signal and the skin surface temperature.

The first distance may be 5 mm or less, and the second distance may be 15 mm or less.

BRIEF DESCRIPTION OF THE DRAWINGS

The above and/or other aspects will be more apparent by describing certain example embodiments, with reference to the accompanying drawings, in which.

DETAILED DESCRIPTION

Figure 1A:
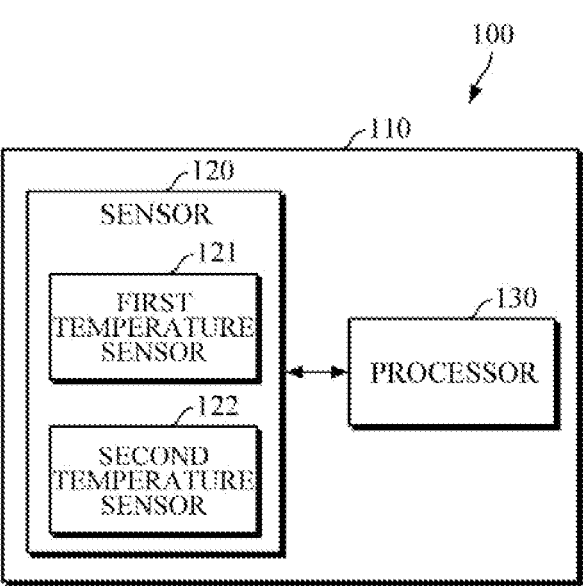
FIGS. 1A and 1B are a block diagram and a structure of an electronic device according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

An electronic device according to various embodiments of the present disclosure which will be described below may include, for example, at least one of a wearable device, a smartphone, a tablet PC, a mobile phone, a video phone, an electronic book reader, a desktop computer, a laptop computer, a netbook computer, a workstation, a server, a PDA, a portable multimedia player (PMP), an MP3 player, a medical device, and a camera. The wearable device may include at least one of an accessory type wearable device (e.g., wristwatch, ring, bracelet, anklet, necklace, glasses, contact lens, or head mounted device (HMD)), a textile/clothing type wearable device (e.g., electronic clothing), a body-mounted type wearable device (e.g., skin pad or tattoo), and a body implantable type wearable device. However, the wearable device is not limited thereto and may include, for example, various portable medical measuring devices (antioxidant measuring device, blood glucose monitor, heart rate monitor, blood pressure measuring device, thermometer, etc.), magnetic resonance angiography (MRA), magnetic resonance imaging (MRI), computed tomography (CT), imaging system, ultrasonic system, etc.), and the like. However, the electronic device is not limited to the above devices.

Figure 1B:
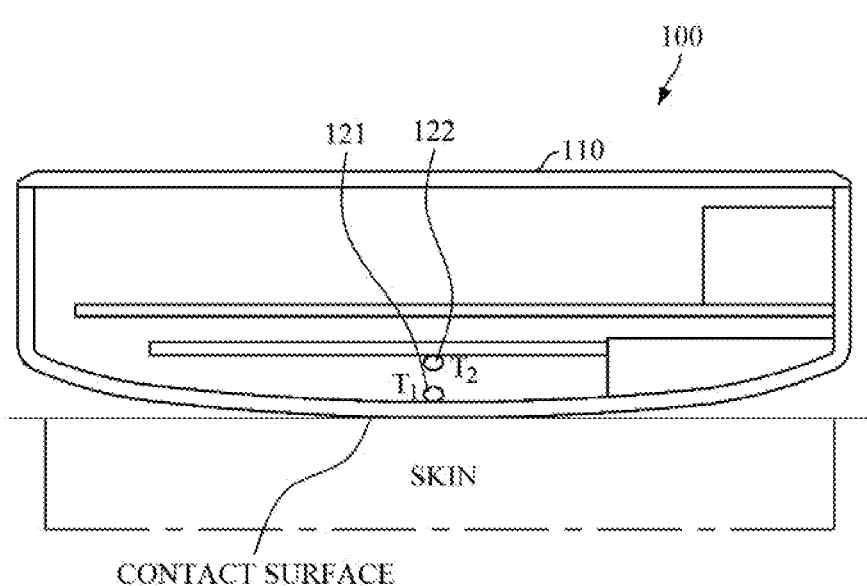
Figure 2A:
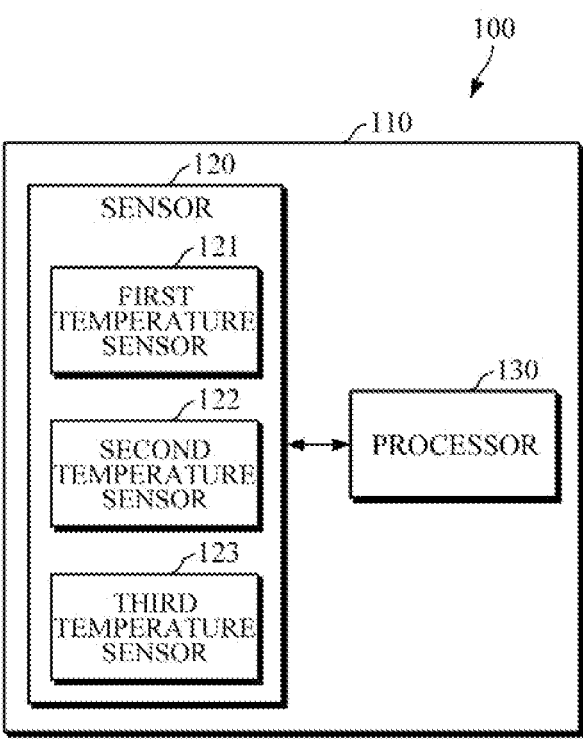
FIGS. 2A and 2B are a block diagram and a structure of an electronic device according to an embodiment of the present disclosure.
Figure 2B:
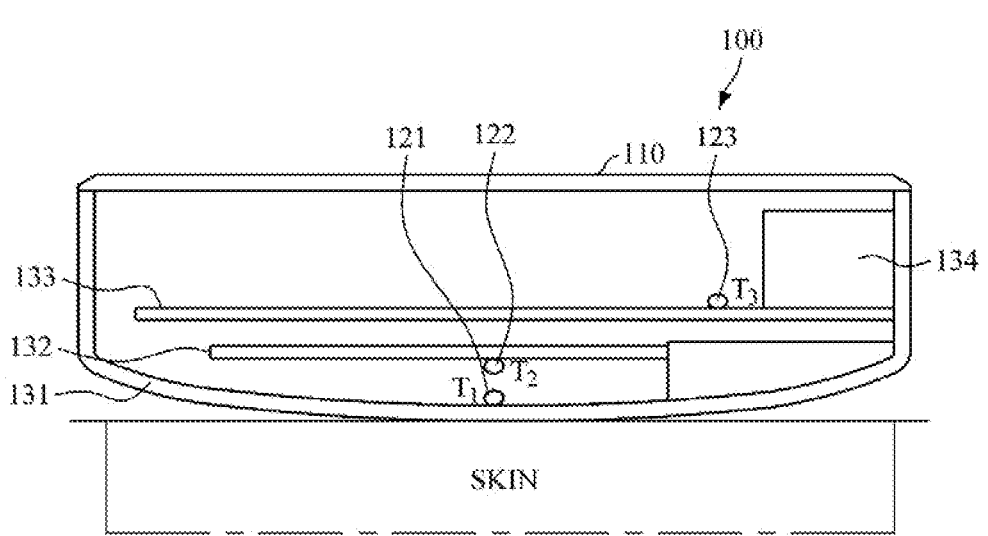

FIGS. 1A and 1B are a block diagram and a structure of an electronic device according to an embodiment of the present disclosure. FIGS. 2A and 2B are a block diagram and a structure of an electronic device according to an embodiment of the present disclosure.

Referring to FIG. 1A, an electronic device 100 includes a sensor 120 and a processor 130 which are mounted in a main body 110. The sensor 120 may include a plurality of temperature sensors and may obtain data for estimating skin surface temperature. The processor 130 may estimate the skin surface temperature of an object (e.g., a user of the electronic device 100) by using the data obtained by the sensor 120.

The sensor 120 may include a first temperature sensor 121 and a second temperature sensor 122, and the first temperature sensor 121 and the second temperature sensor 122 may be disposed at different positions in the main body 110. Referring to FIG. 1B, the first temperature sensor 121 may be disposed, for example, on or in proximity to a contact surface which is to be in contact with a skin surface of the object and may measure a first temperature $T_1$ when the object comes into contact with the main body 110, and the second temperature sensor 122 may be spaced apart from the first temperature sensor 121 in a direction opposite the contact surface and may measure a second temperature $T_2$. For example, the first temperature sensor 121 may be disposed on a back cover 131 of the electronic device 100, and the second temperature sensor 122 may be disposed on a logic board (e.g., a printed circuit board) 132, although the locations of the first temperature sensor 121 and the second temperature sensor 131 are not limited thereto. The first temperature sensor 121 and the second temperature sensor 122 may be disposed apart from each other in a depth direction of the electronic device (e.g., being disposed in a straight line). In addition, the first temperature sensor 121 may be disposed at a distance of 5 mm or less from the skin surface, and a distance between the first temperature sensor 121 and the second temperature sensor 122 may be 10 mm or less. By providing the first temperature sensor 121 in closest possible proximity to the skin surface, the accuracy of skin surface temperature may increase. The arrangement of the first temperature sensor 121 and the second temperature sensor 122 is not limited thereto. In this case, at least one of the first temperature sensor 121 and the second temperature sensor 122 may be a thermistor.

The processor 130 may be electrically connected to the sensor 120 and may control the sensor 120 in response to a request for estimating skin surface temperature.

The processor 130 may estimate the skin surface temperature by using the first temperature $T_1$, obtained by the first temperature sensor 121, and the second temperature $T_2$ obtained by the second temperature sensor 122. In this case, the processor 130 may detect a temperature change due to heat generation inside the main body 110, and may estimate the skin surface temperature by using the first temperature $T_1$ and the second temperature $T_2$ based on a temperature change detection result.

Generally, components, such as a sensor (e.g., photoplethysmography (PPG) sensor) or an application processor (AP), are included in an electronic device, and the components generate heat during operation of the electronic device, such that temperature measurement may be distorted. Accordingly, in order to accurately estimate the skin surface temperature, it is required to reflect heat generation inside the device during the estimation.

First, the processor 130 may detect a temperature change due to heat generation inside the main body 110.

For example, the processor 130 may detect a temperature change due to heat generation inside the main body 110 based on at least one of a variation in the measured first temperature $T_1$ compared to a first reference temperature, and a variation in the measured second temperature $T_2$ compared to a second reference temperature.

For example, if at least one of the following conditions is satisfied: the variation in the measured first temperature $T_1$ compared to the first reference temperature is greater than or equal to a predetermined first threshold value; and the variation in the measured second temperature $T_2$ compared to the second reference temperature is greater than or equal to a predetermined second threshold value, the processor 130 may determine that there is a temperature change due to heat generation inside the main body 110, which may be represented by the following Equations 1 and 2.

$$\frac{T_{1,t2} - T_{1,t1}}{t2 - t1} \geq \varepsilon \qquad \text{[Equation 1]}$$

$$\frac{T_{2,t2} - T_{2,t1}}{t2 - t1} \geq \theta \qquad \text{[Equation 2]}$$

Herein, $T_{1,t2}$ denotes the first temperature $T_1$ measured at time t2, $T_{1,t1}$ denotes the first temperature $T_1$ measured at time t1 which is a measurement time of a reference value, i.e., the first reference temperature. In addition, $T_{2,t2}$ denotes the second temperature $T_2$ measured at time t2, and $T_{2,t1}$ denotes the second temperature $T_2$ measured at time t1 which is a measurement time of a reference value, i.e., the second reference temperature. Further, $\varepsilon$ and $\theta$ denote the first threshold value and the second threshold value, respectively.

For example, if a variation between a first temperature during measurement of the skin surface temperature and a first temperature measured before a predetermined period of time (e.g., one minute) is greater than or equal to a predetermined threshold value, or if a variation between a second temperature during measurement of the skin surface temperature and a second temperature measured before a predetermined period of time (e.g., one minute) is greater than or equal to a predetermined threshold value, the processor 130 may determine that there is a temperature change due to heat generation inside the main body 110.

Then, upon determining that there is a temperature change, the processor 130 may determine the first temperature and the second temperature to be outliers, and upon determining the outliers, the processor 130 may terminate measurement of the skin surface temperature or may guide a user to re-measure after a lapse of a predetermined period of time. For example, in order not to reflect the outliers in measurement, the processor 130 may terminate the estimation of the skin surface temperature. In addition, in order to reduce the effect of heat generation, the processor 130 may guide a user to re-measure after a lapse of a predetermined period of time by outputting, for example, a text such as "please re-measure in five minutes," to a display of the electronic device. In this case, a method of guiding the user is not limited thereto.

Figure 3:
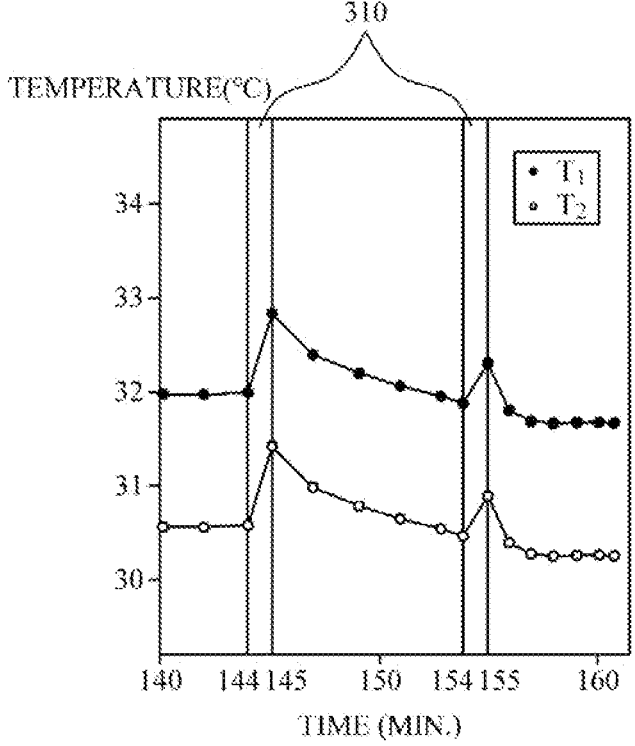
FIG. 3 is a graph showing a change in first temperature and second temperature over time during measurement of skin surface temperature.

FIG. 3 is a graph showing a change in the first temperature and the second temperature over time during measurement of the skin surface temperature.

Referring to FIG. 3, in a case 310 where heat is generated by a component (e.g., PPG sensor) inside an electronic device in an interval between 144 and 145 minutes and an interval between 154 and 155 minutes after measurement, it can be seen that the first temperature $T_1$ and the second temperature $T_2$ rapidly rise. In this case, if at least one of a temperature variation in the interval between 144 and 145 minutes and a temperature variation in the interval between 154 and 155 minutes is greater than or equal to a predetermined threshold value, the processor 130 may determine a measured value to be an outlier, and may terminate the measurement of the skin surface temperature and may guide a user to re-measure the temperature.

In another example, referring to FIGS. 2A and 2B, the electronic device 100 may further include, for example, a third temperature sensor 123 disposed inside the main body 110 and configured to measure a third temperature $T_3$ when heat is generated inside the main body 110. The third temperature sensor 123 may be disposed downward at a vertical distance of 10 mm or less from an upper surface of the main body 110. In addition, a distance between the third temperature sensor 123 and the second temperature sensor 122 may be 50 mm or less. In this case, the third temperature sensor 123 may be attached to a layer 133 (e.g., a sensor circuit board, a substrate including AP or a battery 134, a display assembly including a touch detection layer, a force sensitive layer, a display layer, or a battery) that generates heat at a predetermined temperature inside the main body 110. The arrangement of the third temperature sensor is not limited thereto. Furthermore, the third temperature sensor 123 may be a thermistor.

First, the processor 130 may detect a temperature change due to heat generation inside the main body 110 based on a ratio of a difference between the first temperature $T_1$ and the second temperature $T_2$ and a difference between the first temperature $T_1$ and the third temperature $T_3$.

For example, if the ratio is greater than or equal to a predetermined third threshold value when the first temperature $T_1$ is higher than the third temperature $T_3$, or if the ratio is less than or equal to a predetermined fourth threshold value when the third temperature $T_3$ is higher than the first temperature $T_1$, the processor 130 may determine that there is a temperature change due to heat generation inside the main body 110, which may be represented by the following Equations 3 and 4.

$$\frac{T_1 - T_2}{T_1 - T_3} \geq \gamma \quad \text{if } T_1 > T_3 \qquad \text{[Equation 3]}$$

$$\frac{T_1 - T_2}{T_1 - T_3} \geq \delta \quad \text{if } T_1 < T_3 \qquad \text{[Equation 4]}$$

Herein, r and a denote the predetermined third threshold value and fourth threshold value, respectively, in which r may be a value greater than a.

In another example, the processor 130 may detect the temperature change due to heat generation inside the main body 110 based on a ratio of a difference between the first temperature $T_1$ and the second temperature $T_2$ and a difference between the second temperature $T_2$ and the third temperature $T_3$.

For example, if the ratio is greater than or equal to a predetermined fifth threshold value when the second temperature $T_2$ is higher than the third temperature $T_3$, or if the ratio is less than or equal to a predetermined sixth threshold value when the third temperature $T_3$ is higher than the second temperature $T_2$, the processor 130 may determine that there is a temperature change due to heat generation inside the main body 110, which may be represented by the following Equations 5 and 6.

$$\frac{T_1 - T_2}{T_2 - T_3} \geq \alpha \quad \text{if } T_2 > T_3 \qquad \text{[Equation 5]}$$

-continued $$\frac{T_1 - T_2}{T_2 - T_3} \leq \beta \quad \text{if } T_2 < T_3 \qquad \text{[Equation 6]}$$

Herein, $\alpha$ and $\beta$ denote the predetermined fifth threshold value and sixth threshold value, respectively, in which a may be a value greater than 3.

In this case, the threshold values may be in the form of a function, rather than predetermined numbers. For example, the threshold values may be expressed as a function that varies according to an interval between measurement time points, which may be represented by the following Equations 7 and 8.

$$\frac{(T_{1,t2} - T_{2,t2})}{(T_{1,t2} - T_{3,t2})} - \frac{(T_{1,t1} - T_{2,t1})}{(T_{1,t1} - T_{3,t1})} \geq \gamma(t2 - t1) \quad \text{if } T_{1,t2} > T_{3,t2} \qquad \text{[Equation 7]}$$

$$\frac{(T_{1,t2} - T_{2,t2})}{(T_{1,t2} - T_{3,t2})} - \frac{(T_{1,t1} - T_{2,t1})}{(T_{1,t1} - T_{3,t1})} \leq \delta(t2 - t1) \quad \text{if } T_{1,t2} < T_{3,t2} \qquad \text{[Equation 8]}$$

Herein, $T_{1,t2}$ denotes the first temperature $T_1$ measured at time t2, and $T_{1,t1}$ denotes the first temperature $T_1$ measured at time t1 which is a measurement time of a reference value, i.e., the first reference temperature. In addition, $T_{2,t2}$ denotes the second temperature $T_2$ measured at time t2, and $T_{2,t1}$ denotes the second temperature $T_2$ measured at time t1 which is a measurement time of a reference value, i.e., the second reference temperature. Also, $T_{3,t2}$ denotes the third temperature $T_3$ measured at time t2, and $T_{3,t1}$ denotes the third temperature $T_3$ measured at time t1 which is a measurement time of a reference value, i.e., the reference third temperature.

The above Equation 7 may indicate that a value, obtained by dividing a difference between a ratio of temperature differences between the temperature sensors at time t2 and a ratio of temperature differences between the temperature sensors at time t1, which is a measurement time of a reference value, by a measurement time interval, is greater than or equal to a threshold value; and the above Equation 8 may indicate that a value, obtained by dividing a difference between a ratio of temperature differences between the temperature sensors at time t2 and a ratio of temperature differences between the temperature sensors at time t1, which is a measurement time of a reference value, by a measurement time interval, is a smaller than or equal to a threshold value.

Based on the arrangement of the first temperature sensor 121 and the second temperature sensor 122, the processor 130 may classify heat generating components in the main body 110 into a plurality of groups according to position, and may determine the third threshold value and the fourth threshold value differently for each of the groups. For example, the processor 130 may determine a group of components which are in operation when the skin surface temperature is measured, and may determine whether there is a temperature change due to heat generation by applying the third threshold value and the fourth threshold value corresponding to the determined group.

Figure 4:
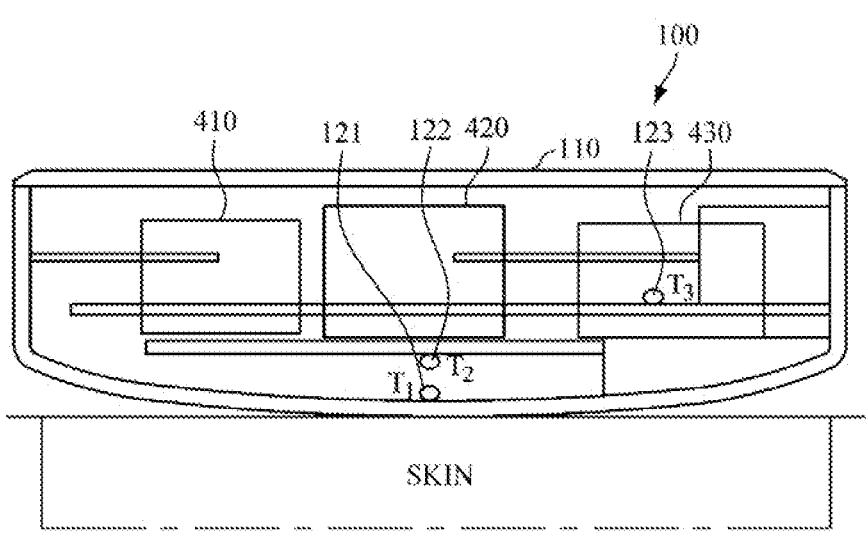
FIG. 4 is a diagram illustrating an example of dividing components in a main body into a plurality of groups.

FIG. 4 is a diagram illustrating an example of dividing the components in the main body into a plurality of groups.

Referring to FIG. 4, the processor 130 may divide, for example, components disposed at an upper side of the first temperature sensor 121 and the second temperature sensor into a first group 410, a second group 420, and a third group 430, and may determine in advance the third threshold value and the fourth threshold value differently for each group. Assuming that the components in the first group 410 are in operation when the skin surface temperature is measured, the components in the first group 410 generate heat inside the main body 110, such that the processor 130 may determine whether there is a temperature change due to heat generation by using the third threshold value and the fourth threshold value corresponding to the first group 410. By applying different values to each group as described above, there is no need to provide a plurality of third temperature sensors, and the processor 130 may determine whether there is a temperature change due to heat generation regardless of position of the third temperature sensor.

Then, upon determining that there is the temperature change, the processor 130 may correct the first temperature $T_1$ and the second temperature $T_2$ based on the measured third temperature $T_3$. In this case, the processor 130 may correct the first temperature $T_1$ and the second temperature $T_2$ by subtracting the effect of heat inflow from each of the first temperature $T_1$ and the second temperature $T_2$ inside the main body 110, which may be represented by the following Equations 9 to 13.

$$T_{in} = \mu(T_{3spike}) \qquad \text{[Equation 9]}$$

Herein, $T_{3spike}$ denotes a third temperature when heat is generated, p denotes a rate of heat loss of transferred heat, $T_{in}$ denotes the transferred heat. The heat generated by the components is transferred by conduction and decreases in proportion to distance between a heating source and the first temperature sensor 121 until the heat flows into the first temperature sensor 121. The heat which decreases linearly with distance may be represented by Equation 9, and the heat which decreases non-linearly with distance may be represented by the following Equation 10.

$$T_{in} = f(T_{3spike}, d) \qquad \text{[Equation 10]}$$

Herein, f denotes a heat loss function, and d denotes a distance between a heat generating component (e.g., a battery, a PPG sensor, or a logic board including a processor) and the first temperature sensor 121.

When the heat flows into the first temperature sensor 121, the first temperature $T_1$ is determined by adding the heat, generated from the heat generating component, to heat generated from skin to be measured. In order to identify the heat generated from the skin, it is required to subtract heat, transferred from the heat generating component, from the first temperature $T_1$. When heat at a temperature of $T_{in}$ is transferred from the heat generating component, the transferred heat gradually spreads around over time to achieve heat balance. Diffusion of the transferred heat may be estimated using Equations 11 to 13 based on Newton's law of cooling.

$$T_{1t} = T_{1c} + (T_{1c} + T_{in} - T_{1c})e^{-k_1 \tau} \qquad \text{[Equation 11]}$$

$$T_{1c} = T_{1t} - T_{in}e^{-k_1 \tau} \qquad \text{[Equation 12]}$$

$$T_{2c} = T_{2t} - T_{in}e^{-k_2 \tau} \qquad \text{[Equation 13]}$$

Herein, $T_{1c}$ denotes temperature obtained by subtracting the effect of heat inflow from the first temperature $T_{1t}$ measured at time t, and $T_{2c}$ denotes temperature obtained by subtracting the effect of heat inflow from the second temperature $T_{2t}$ measured at time t. The effect of heat inflow may be represented as $T_{in}e^{-k_1 \tau}$ and $T_{in}e^{-k_2 \tau}$, which indicate heat that is transferred from the heat generating component to the first temperature sensor and the second temperature sensor, respectively. The amount of heat transferred from the heat generating component may decrease as it travels from the heat generating component to a corresponding temperature sensor along a heat transfer path between the heat generating element and the corresponding temperature sensor, as shown by Equations 12 and 13. $K_1$ and $K_2$ denote diffusion constants of heat flowing into the first temperature sensor and the second temperature sensor, respectively, and $\tau$ denotes elapsed time after the heat inflow. That is, finally obtained $T_{1c}$ and $T_{2c}$ correspond to the corrected first temperature and the corrected second temperature, respectively.

Then, the processor 130 may estimate the skin surface temperature based on a difference between the corrected first temperature $T_{1c}$ and the corrected second temperature $T_{2c}$.

Figure 5:
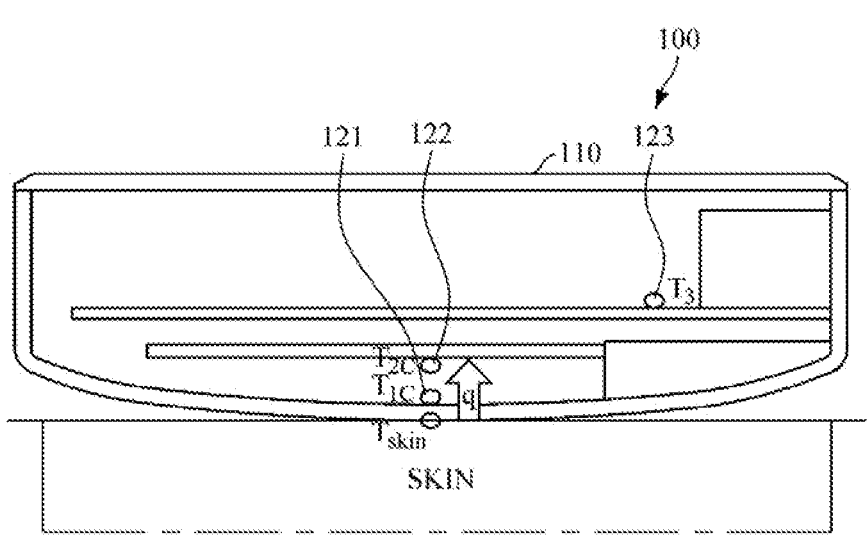
FIGS. 5 and 6 are diagrams illustrating an example of estimating skin surface temperature.
Figure 6:
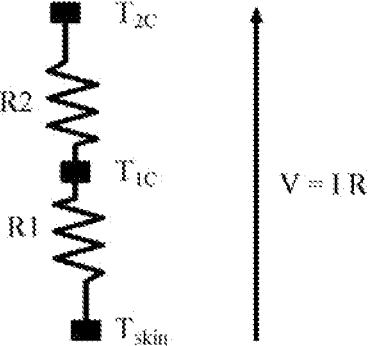

FIGS. 5 and 6 are diagrams illustrating an example of estimating skin surface temperature.

Referring to FIGS. 5 and 6, a difference between skin surface temperature $T_{skin}$ of an object and the corrected first temperature $T_{1c}$ may be expressed as heat flux q. In addition, assuming heat transfer from the skin surface in a series circuit, the same heat flux q may also be estimated from a temperature difference $(T_{1c}-T_{2c})$ between the corrected first temperature $T_{1c}$ and the corrected second temperature $T_{2c}$. In this case, with respect to heat transfer from the skin surface to the second temperature sensor 122, the following Equation 14 may be derived based on Ohm's law (V=IR).

$$I = \frac{T_{skin} - T_{1c}}{R_1} = \frac{T_{1c} - T_{2c}}{R_2} \qquad \text{[Equation 14]}$$

Herein, $R_1$ denotes a predetermined thermal resistance between the skin surface and the first temperature sensor 121, $R_2$ denotes a predetermined thermal resistance between the first temperature sensor 121 and the second temperature sensor 122, and I denotes a thermoelectric current, in which $R_1$ may be obtained by multiplying the reciprocal of thermal conductivity for a material of an object, disposed between the skin surface and the first temperature sensor 121, by a distance between the skin surface and the first temperature sensor 121, and $R_2$ may be obtained by multiplying the reciprocal of thermal conductivity between the first temperature sensor 121 and the second temperature sensor 122 by a distance between the first temperature sensor 121 and the second temperature sensor 122. In this case, glass with high thermal conductivity (thermal conductivity of about 1.1 W/m° C.) may be disposed between the skin surface and the first temperature sensor 121, and air with very low thermal conductivity (thermal conductivity of about 0.023 W/m° C.) may also be disposed between the first temperature sensor 121 and the second temperature sensor 122.

Lastly, the skin surface temperature may be represented by the following Equation 15 based on Equation 14.

$$T_{skin} = T_{1c} + \frac{T_{1c} - T_{2c}}{R_2/R_1} \qquad \text{[Equation 15]}$$

Figure 7:
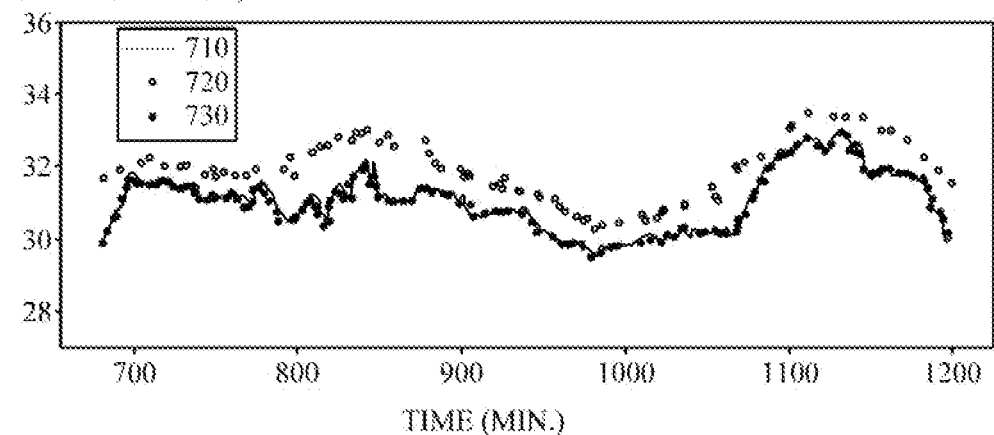
FIG. 7 is a graph showing skin surface temperature values estimated over time in the case where a first temperature and a second temperature are used, and in the case where a corrected first temperature and a corrected second temperature are used.

FIG. 7 is a graph showing skin surface temperature values estimated over time in the case where the first temperature and the second temperature are used, and in the case where the corrected first temperature and the corrected second temperature are used.

Referring to FIG. 7, for example, when heat generation by a component (e.g., AP) is detected inside the main body 110, in comparison of an actually measured skin surface temperature 710 with a case 720 where the skin surface temperature is measured over time by measuring the first temperature and the second temperature regardless of the effect of heat generation and a case 730 where the skin surface temperature is measured over time based on the corrected first temperature and the corrected second temperature in consideration of the effect of heat generation, it can be seen that the case 730 where the skin surface temperature is measured based on the corrected first temperature and the corrected second temperature is more similar to the actually measured skin surface temperature 710.

Figure 8:
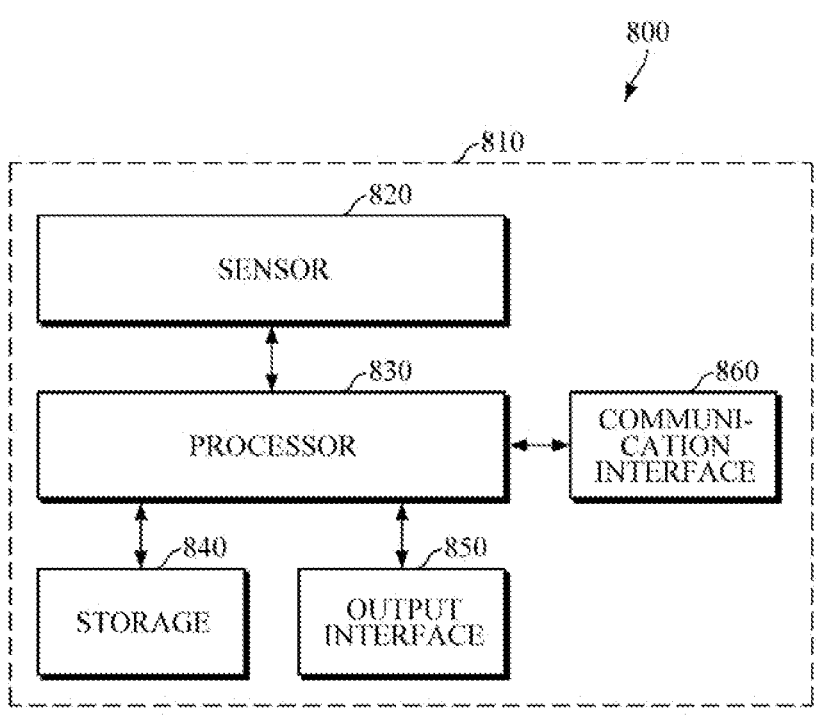
FIG. 8 is a block diagram illustrating an electronic device for estimating skin surface temperature according to an embodiment of the present disclosure.

FIG. 8 is a block diagram illustrating an electronic device for estimating skin surface temperature according to another embodiment of the present disclosure.

Referring to FIG. 8, an electronic device 800 includes a sensor 820, a processor 830, a storage 840, an output interface 850, and a communication device 860, which are mounted in a main body 810. In this case, the sensor 820 and the processor 830 are the same as the sensor 120 and the processor 130 in the embodiments of FIGS. 1A and 2A, such that a detailed description thereof will be omitted.

The storage 840 may store information related to estimating skin surface temperature. For example, the storage 840 may store temperature data, a threshold value for detecting a temperature change due to heat generation, and a rate of heat loss of transferred heat, which are obtained by the sensor 820, and processing results of the processor 830, e.g., corrected temperature data, estimated skin surface temperature, and the like. In this case, the threshold value or the rate of heat loss of the transferred heat are not constants but may be expressed as a function that varies with time.

The storage 840 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 850 may provide a user with the processing results of the processor 830. For example, the output interface 850 may display the skin surface temperature estimated by the processor 830 on a display. In this case, the output interface 850 may provide a user with the estimated skin surface temperature value by changing color, line thickness, etc., so that the user may easily recognize the estimated skin surface temperature value, and may provide the user with information on a change in continuous skin surface temperature values over time. In addition, the output interface 850 may output information on at least one of the first temperature, second temperature, third temperature, corrected first temperature, corrected second temperature, and skin surface temperature to the display. Furthermore, when the measured temperature is determined to be an outlier, the output interface 850 may output guidance on re-measurement after a lapse of a predetermined period of time, e.g., a text such as "please re-measure in five minutes," to the display. In addition, along with or without the visual display, the output interface 850 may provide the user with information on the skin surface temperature in a non-visual manner by voice, vibrations, tactile sensation, and the like using an audio output module such as a speaker, or a haptic module, and the like.

The communication interface 860 may communicate with an external device to transmit and receive various data related to estimating the skin surface temperature. The external device may include an information processing device, such as a smartphone, a tablet PC, a desktop computer, a laptop computer, and the like. For example, the communication interface 860 may transmit a skin surface temperature measurement result to an external device such as a smartphone and the like, and a user may monitor the skin surface temperature over time by using, e.g., the smartphone.

The communication interface 860 may communication with the electronic device by using various wired and wireless communication techniques including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, 5G, and 6G communications, and the like. However, the communication techniques are not limited thereto.

Figure 9:
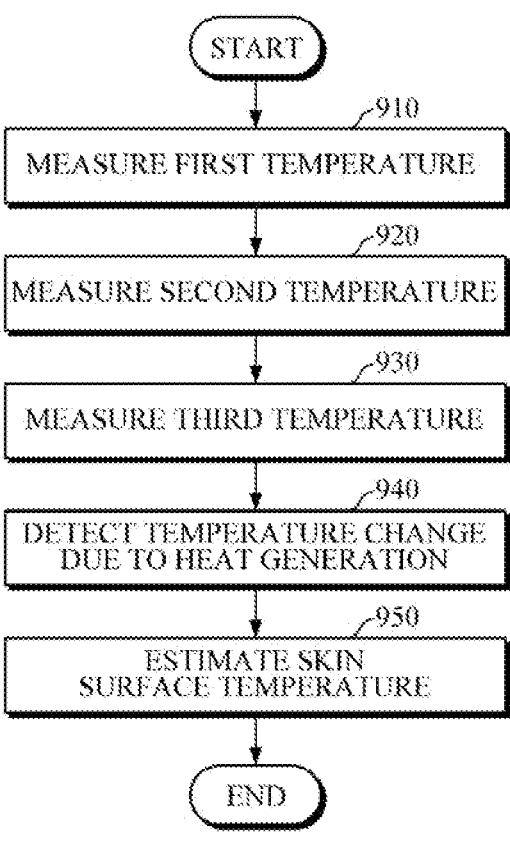
FIG. 9 is a flowchart illustrating a method of estimating skin surface temperature according to an embodiment of the present disclosure.

FIG. 9 is a flowchart illustrating a method of estimating skin surface temperature according to an embodiment of the present disclosure.

The method of FIG. 9 is an example of a method of estimating skin surface temperature performed by the electronic devices 100 and 800, which are described in detail above, and thus will be briefly described below in order to avoid redundancy.

Referring to FIG. 9, the electronic device may measure a first temperature by using the first temperature sensor disposed in proximity to a skin surface when an object comes into contact with the main body in operation 910, and may measure a second temperature by using the second temperature sensor spaced apart from the first temperature sensor in a direction opposite the skin surface in operation 920. In addition, by using the third temperature sensor disposed in the main body, the electronic device may further measure a third temperature when heat is generated inside the main body in operation 930. The order of measuring the first temperature, the second temperature, and the third temperature may not be limited to the order illustrated in FIG. 9. For example, the first temperature, the second temperature, and the third temperature may be measured at the same time, or may be measured in an order different from the order illustrated in FIG. 9.

Then, the electronic device may detect a temperature change due to heat generation inside the main body in operation 940.

The electronic device may detect a temperature change due to heat generation inside the main body based on at least one of a variation in the measured first temperature compared to a first reference temperature, and a variation in the measured second temperature compared to a second reference temperature. For example, if at least one of the following conditions is satisfied: the variation in the measured first temperature is greater than or equal to a predetermined first threshold value; and the variation in the measured second temperature is greater than or equal to a predetermined second threshold value, the processor 130 may determine that there is a temperature change due to heat generation inside the main body.

In addition, the electronic device may detect a temperature change due to heat generation inside the main body based on a ratio of a difference between the first temperature and the second temperature and a difference between the first temperature and the third temperature. For example, if the ratio is greater than or equal to a predetermined third threshold value when the first temperature is higher than the third temperature, or if the ratio is less than or equal to a predetermined fourth threshold value when the third temperature is higher than the first temperature, the electronic device may determine that there is a temperature change due to heat generation inside the main body.

Subsequently, the electronic device may estimate the skin surface temperature by using the first temperature and the second temperature based on a temperature change detection result in operation 950.

For example, upon determining that there is the temperature change due to heat generation inside the main body based on the variation in the first temperature that is greater than or equal to the predetermined first threshold value, or the variation in the second temperature that is greater than or equal to the predetermined second threshold value, the electronic device may determine the first temperature and the second temperature to be outliers, and may terminate measurement of the skin surface temperature or may guide a user to re-measure after a lapse of a predetermined period of time.

In addition, upon determining that there is the temperature change due to heat generation inside the main body based on the ratio that is greater than or equal to the predetermined third threshold value when the first temperature is higher than the third temperature, or the ratio that is less than or equal to the predetermined fourth threshold value when the third temperature is higher than the first temperature, the electronic device may correct the first temperature and the second temperature based on the measured third temperature, and may estimate the skin surface temperature based on a difference between the corrected first temperature and the corrected second temperature.

FIGS. 10 to 13 are diagrams illustrating examples of structures of an electronic device.

Figure 10:
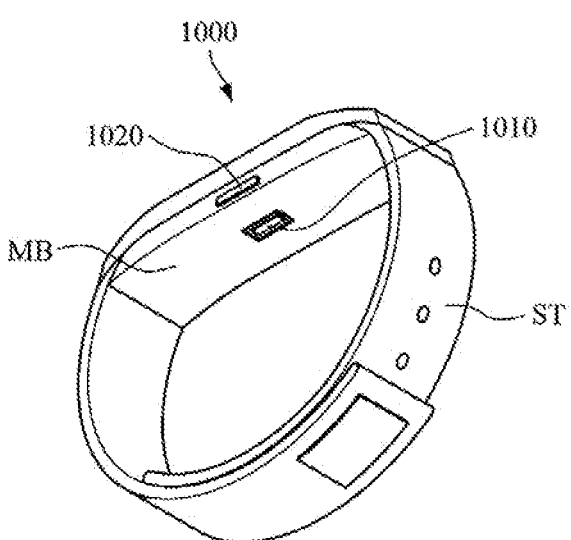
FIGS. 10 to 13 are diagrams illustrating examples of structures of an electronic device.

Referring to FIG. 10, the electronic device may be implemented as a smart watch wearable device 1000 including a main body MB and a wrist strap ST.

The main body MB may be formed in various shapes. A battery may be embedded in the main body MB and/or the strap ST to supply power to various components of the wearable device. The strap ST may be connected to both ends of the main body to allow the main body to be worn on a user's wrist, and may be flexible so as to be wrapped around the user's wrist. The strap ST may be composed of a first strap and a second strap which are separated from each other. One end of each of the first strap and the second strap may be connected to both sides of the main body MB, and the first and second straps may be connected to each other via a fastening means formed at the other ends thereof. In this case, the fastening means may be formed as magnetic fastening, Velcro fastening, pin fastening, etc., but is not limited thereto. Further, the strap ST is not limited thereto, and may be integrally formed as a non-detachable band.

The main body MB may include a sensor 1010, a processor, an output interface, a storage, and a communication interface. However, some of the output interface, storage, and the communication interface may be omitted depending on the size and shape of a form factor and the like.

The sensor 1010 may include a plurality of sensors disposed at different distances from a skin surface. For example, the first temperature sensor may be disposed in proximity to the skin surface and may measure a first temperature when the object comes into contact with the main body, and the second temperature sensor may be spaced apart from the first temperature sensor in a direction opposite the skin surface and may measure a second temperature. In addition, a third temperature sensor may measure a third temperature when heat is generated inside the main body, and may be attached to, for example, a component in the main body. In this case, the sensor 1010 may be disposed on a rear surface of the main body MB, so that when the main body MB is worn on a user's wrist, the sensor 1010 may come into contact with an upper part of the user's wrist to obtain data for measuring the skin surface temperature.

The processor mounted in the main body MB may be electrically connected to various components as well as the sensor 1010. The processor may estimate the skin surface temperature of a user by using the data obtained by the plurality of temperature sensors. For example, the processor may detect a temperature change due to heat generation inside the main body while the main body MB is worn, and may estimate the skin surface temperature by using temperatures measured by the plurality of temperature sensors.

A display may be provided on a front surface of the main body MB and may display various application screens, including skin surface temperature information, time information, received message information, and the like. For example, the processor may display an estimated skin surface temperature value on the display. In this case, if an estimated skin surface temperature value falls outside a normal range, the processor may provide the user with warning information by changing color, line thickness, etc., or displaying an abnormal value along with the normal range, so that the user may easily recognize the abnormal value. In addition, in response to the user's request, the processor may display and provide not only a current estimated skin surface temperature value, but also continuous estimated skin surface temperature values over time on the display for the user. In addition, the processor may display a skin surface temperature variation, for example, a skin surface temperature change during a day, in a graph on the display, and may also display information on sleep quality based on the skin surface temperature change on the display. The information which may be displayed on the display may include not only the skin surface temperature information, but also the first temperature, second temperature, third temperature, corrected first temperature, corrected second temperature, skin surface temperature guidance information, etc., but is not limited thereto.

In another example, the wearable device worn by a user and configured to estimate skin surface temperature may include: a main body MB; a first temperature sensor disposed in the main body at a position spaced apart from a skin surface by a first distance without contact with the skin surface when the wearable device is worn by the user; a second temperature sensor disposed in the main body at a position spaced apart from the skin surface by a second distance, which is greater than the first distance, when the wearable device is worn by the user; and a processor disposed in the main body and configured to estimate skin surface temperature by using a first temperature measured by the first temperature sensor and a second temperature measured by the second temperature sensor.

In addition, the wearable device may further include a third temperature sensor disposed in the main body at a position spaced apart from the skin surface by a third distance, which is greater than the second distance, when the wearable device is worn by the user. In this case, the first distance may be, e.g., 5 mm or less, the second distance may be, e.g., 15 mm or less, and the third distance may be, e.g., 65 mm or less.

In this case, the processor may correct the first temperature and the second temperature by using the third temperature measured by the third temperature sensor when heat is generated inside the main body, and may estimate the skin surface temperature based on a difference between the corrected first temperature and the corrected second temperature.

In addition, the main body may further include a display, so that the estimated skin surface temperature may be displayed on the display. Also, the main body may further include a PPG sensor for measuring a bio-signal of an object.

Figure 11:
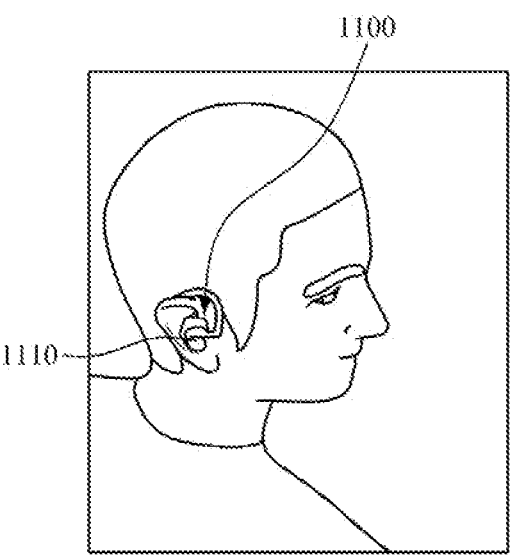

Referring to FIG. 11, the electronic device may be implemented as an ear-wearable device 1100.

The ear-wearable device 1100 may include a main body and an ear strap. A user may wear the ear-wearable device 1100 by hanging the ear strap on the user's auricle. The ear strap may be omitted depending on the shape of the ear-wearable device 1100. The main body may be inserted into the external auditory meatus. A sensor 1110 may be mounted in the main body. The ear-wearable device 1100 may provide a user with an estimation result of the skin surface temperature as sound, or may transmit the estimation result to an external device, e.g., mobile device, tablet PC, etc., through a communication module provided in the main body.

Figure 12:
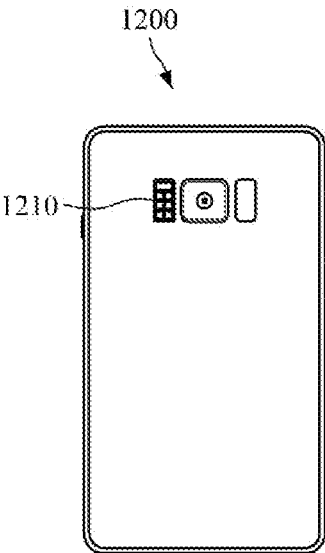

Referring to FIG. 12, the electronic device may be implemented as a mobile device 1200 such as a smartphone.

The mobile device 1200 may include a housing and a display panel. The housing may form an outer appearance of the mobile device 1200. The housing has a first surface, on which a display panel and a cover glass may be disposed sequentially, and the display panel may be exposed to the outside through the cover glass. A sensor 1210, a camera module and/or an infrared sensor, and the like may be disposed on a second surface of the housing.

For example, a plurality of temperature sensors for obtaining data from a user may be disposed on a rear surface of the mobile device 1200, and a fingerprint sensor disposed on the front surface of the mobile device 1200, a power button or a volume button disposed on a side surface thereof, sensors disposed at other positions on the front and rear surfaces of the mobile device 1200, and the like may be provided to estimate skin surface temperature.

In addition, when a user transmits a request for estimating the skin surface temperature by executing an application and the like installed in the mobile device 1200, the mobile device 1200 may obtain data by using the sensor 1210, and may estimate the skin surface temperature and provide the estimated value to the user as image and/or sound by using the processor in the mobile device 1200.

Figure 13:
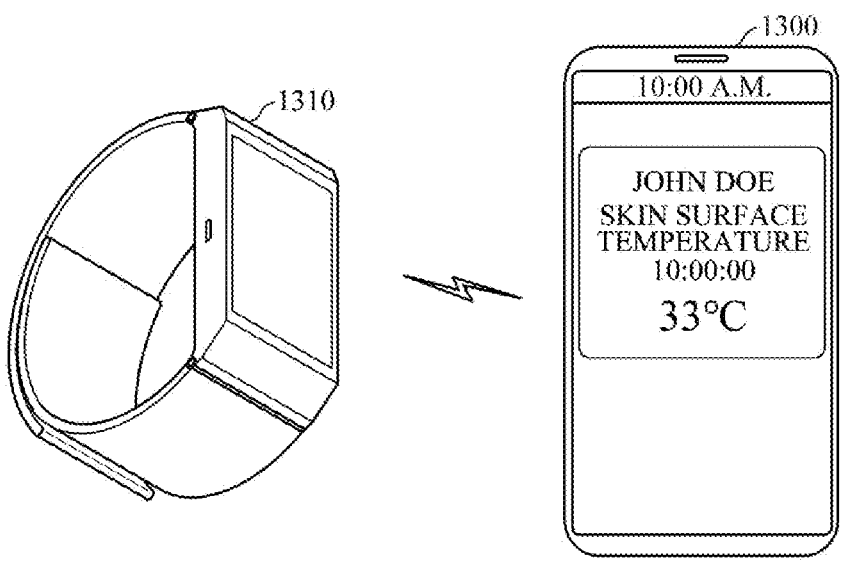

Referring to FIG. 13, the electronic device may be implemented as a combination of a wristwatch-type wearable device and a mobile device such as a smartphone. For example, a memory, a communication interface, and a processor for estimating skin surface temperature may be mounted in a main body of a mobile device 1300. Upon receiving a request for estimating the skin surface temperature, the processor of the mobile device 1300 may control the communication interface to obtain data by communicating with a communication module mounted in a main body of the wearable device 1310. Further, upon receiving data, such as a first temperature, a second temperature, and a third temperature, and the like from the wearable device, the processor may estimate the skin surface temperature, and may output an estimation result to a display of the mobile device through an output interface as illustrated herein.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An electronic device comprising:

a first temperature sensor configured to measure a first temperature at a first position when an object comes into contact with a contact surface of a main body of the electronic device;

a second temperature sensor spaced apart from the first temperature sensor, and configured to measure a second temperature at a second position;

a third temperature sensor disposed inside the main body, and configured to measure a third temperature at a third position when heat is generated inside the main body; and a processor configured to:

detect a temperature change due to heat generation inside the main body based on:

$$\frac{T_{1,t2} - T_{1,t1}}{t_2 - t_1} \text{ and } \frac{T_{2,t2} - T_{2,t1}}{t_2 - t_1}$$

wherein $T_{1,t1}$ and $T_{1,t2}$ denote the first temperatures measured at two different time points $t_1$ and $t_2$, respectively, $T_{2,t1}$ and $T_{2,t2}$ denote the second temperatures measured at the two different time points $t_1$ and $t_2$, respectively;

$$\frac{T_1 - T_2}{T_1 - T_3} \text{ and } \frac{T_1 - T_2}{T_1 - T_3}$$

wherein $T_1$, $T_2$, and $T_3$ denote the first temperature, the second temperature, and the third temperature that are respectively measured at a same time point, which is either the time point $t_1$ or the time point $t_2$; and estimate skin surface temperature based on the first temperature $T_1$, the second temperature $T_2$, the third temperature $T_3$, and the temperature change, wherein the first position is closer to the contact surface of the main body than the second position and the third position, and the third position is closer to a layer comprising or mounting the processor or a battery than the first position and the second position, and the second position is located between the first position and the third position in a thickness direction of the main body.

2. The electronic device of claim 1, wherein a first condition is satisfied when the change in the first temperature $T_1$ is greater than or equal to a predetermined first threshold value, and a second condition is satisfied when the change in the second temperature $T_2$ is greater than or equal to a predetermined second threshold value, and wherein in response to either one or both of the first condition and the second condition is satisfied, the processor is further configured to determine that the temperature change has occurred due to the heat generation inside the main body.

3. The electronic device of claim 2, wherein in response to the temperature change being detected, the processor is further configured to determine the first temperature $T_1$ and the second temperature $T_2$ as outliers.

4. The electronic device of claim 3, wherein in response to the first temperature $T_1$ and the second temperature $T_2$ being determined as the outliers, the processor is further configured to terminate measurement of the first temperature $T_1$ and the second temperature $T_2$, or guide re-measurement of the first temperature $T_1$ and the second temperature $T_2$ after a lapse of a predetermined period of time.

5. The electronic device of claim 1, wherein in response to $$\frac{T_1 - T_2}{T_1 - T_3} \text{ and } \frac{T_1 - T_2}{T_1 - T_3}$$

being greater than or equal to a predetermined third threshold value when the first temperature is higher than the third temperature $T_3$, or in response to $$\frac{T_1 - T_2}{T_1 - T_3} \text{ and } \frac{T_1 - T_2}{T_1 - T_3}$$

being less than or equal to a predetermined fourth threshold value when the third temperature $T_3$ is higher than the first temperature $T_1$, the processor is further configured to determine that the temperature change has occurred due to the heat generation inside the main body.

6. The electronic device of claim 5, wherein upon determining that the temperature change has occurred, the processor is further configured to correct the first temperature $T_1$ and the second temperature $T_2$ based on the third temperature $T_3$.

7. The electronic device of claim 6, wherein the processor is further configured to correct each of the first temperature $T_1$ and the second temperature $T_2$ by subtracting from each of the first temperature $T_1$ and the second temperature $T_2$ in the main body, heat that is transferred from a heat generating component to the first temperature sensor and the second temperature sensor, respectively.

8. The electronic device of claim 7, wherein the processor is further configured to estimate the skin surface temperature based on a difference between the corrected first temperature $T_1$ and the corrected second temperature $T_2$.

9. The electronic device of claim 1, wherein the third temperature sensor is attached to a heat generating component that generates heat at a predetermined temperature inside the main body.

10. The electronic device of claim 1, wherein when the main body of the electronic device is in contact with a skin surface of the object, the first temperature sensor is disposed at a distance of 5 mm or less from the skin surface.

11. A wearable device comprising:

a main body comprising:

a first temperature sensor disposed in the main body at a first position spaced apart from a contact surface of the wearable device by a first distance, and configured to measure a first temperature at the first position;

a second temperature sensor disposed in the main body at a second position spaced apart from the contact surface of the wearable device by a second distance, which is greater than the first distance, and configured to measure a second temperature at the second position;

a third temperature sensor disposed in the main body at a third position spaced apart from the contact surface by a third distance, which is greater than the second distance, and configured to measure a third temperature at the third position; and a processor configured to:

detect a temperature change due to heat generation inside the main body based on:

$$\frac{T_{1,t2} - T_{1,t1}}{t_2 - t_1} \text{ and } \frac{T_{2,t2} - T_{2,t1}}{t_2 - t_1}$$

wherein $T_{1,t1}$ and $T_{1,t2}$ denote the first temperatures measured at two different time points $t_1$ and $t_2$, respectively, $T_{2,t1}$ and $T_{2,t2}$ denote the second temperatures measured at the two different time points $t_1$ and $t_2$, respectively;

$$\frac{T_1 - T_2}{T_1 - T_3} \text{ and } \frac{T_1 - T_2}{T_1 - T_3}$$

wherein $T_1$, $T_2$, and $T_3$ denote the first temperature, the second temperature, and the third temperature that are respectively measured at a same time point, which is either the time point $t_1$ or the time point $t_2$; and estimate skin surface temperature based on the first temperature $T_1$, the second temperature $T_2$, the third temperature $T_3$, and the temperature.

12. The wearable device of claim 11, wherein the processor is further configured to correct the first temperature $T_1$ and the second temperature $T_2$ based on the third temperature $T_3$ measured by the third temperature sensor when heat is generated inside the main body, and estimate the skin surface temperature based on the corrected first temperature $T_1$ and the corrected second temperature $T_2$.

13. The wearable device of claim 11, wherein the third distance is 65 mm or less.

14. The wearable device of claim 11, wherein the main body further comprises a photoplethysmogram (PPG) sensor configured to measure a bio-signal of a user when the wearable device is worn by the user, and the processor is further configured to estimate blood pressure based on the bio-signal and the skin surface temperature.

15. The wearable device of claim 11, wherein the first distance is 5 mm or less, and the second distance is 15 mm or less.

* * * * *